United States Patent
Commereuc et al.

(10) Patent No.: US 6,706,657 B2
(45) Date of Patent: **\*Mar. 16, 2004**

(54) CATALYTIC COMPOSITION FOR DIMERIZING, CO-DIMERIZING AND OLIGOMERIZING OLEFINS

(75) Inventors: Dominique Commereuc, Meudon (FR); Dominique Le Pennec, Orgerus (FR); Hélène Olivier-Bourbigou, Rueil Malmaison (FR)

(73) Assignee: Institut Francais du Petrole, Rueil Malmaison Cedex (FR)

( \* ) Notice: Subject to any disclaimer, the term of this patent is extended or adjusted under 35 U.S.C. 154(b) by 0 days.

This patent is subject to a terminal disclaimer.

(21) Appl. No.: 09/775,556

(22) Filed: Feb. 5, 2001

(65) Prior Publication Data

US 2003/0109766 A1 Jun. 12, 2003

(30) Foreign Application Priority Data

Feb. 4, 2000 (FR) .............................. 00 01512

(51) Int. Cl.⁷ .............................. B01J 31/00; C07C 2/24; C07C 2/02
(52) U.S. Cl. .................. 502/164; 502/162; 502/167; 502/168; 502/169; 502/170; 585/512; 585/513; 585/527
(58) Field of Search ................ 502/162, 164, 502/167, 168, 169, 170; 585/512, 513, 527

(56) References Cited

U.S. PATENT DOCUMENTS

| 5,196,624 A | * | 3/1993 | Threlkel et al. | 585/513 |
|---|---|---|---|---|
| 5,196,625 A | * | 3/1993 | Threlkel et al. | 585/513 |
| 5,365,007 A | * | 11/1994 | Wu | 585/528 |
| 5,502,018 A | * | 3/1996 | Chauvin et al. | 502/162 |
| 5,550,306 A | * | 8/1996 | Chauvin et al. | 585/514 |
| 5,723,712 A | * | 3/1998 | Chauvin et al. | 585/513 |
| 5,744,678 A | * | 4/1998 | Aida et al. | 585/513 |
| 5,750,455 A | * | 5/1998 | Chauvin et al. | 502/164 |
| 6,028,024 A | * | 2/2000 | Hirschauer et al. | 502/162 |
| 6,501,001 B2 | * | 12/2002 | Commereuc et al. | 585/514 |
| 6,576,724 B2 | * | 6/2003 | Olivier-Bourbigou et al. | 502/167 |

FOREIGN PATENT DOCUMENTS

FR 0 646 413 A1 4/1995

OTHER PUBLICATIONS

Grant & Hackh's Chemical Dictionary, 5th ed., McGraw–Hill, p. 438 (no date given).*

\* cited by examiner

Primary Examiner—Elizabeth D. Wood
Assistant Examiner—J. Pasterczyk
(74) Attorney, Agent, or Firm—Millen, White, Zeland & Branigan, P.C.

(57) ABSTRACT

A catalytic composition comprising at least one nickel compound mixed or complexed with at least one tertiary phosphine or a phosphite carrying a functional group, at least partly dissolved in a non-aqueous medium with an ionic nature resulting from bringing at least one aluminum halide into contact with at least one quaternary ammonium halide and/or at least one quaternary phosphonium halide, is useful for dimerizing, co-dimerizing and oligomerizing olefins. Functional groups include, but are not limited to, an amine, a cyclic amine, a nitrogen-containing heterocycle, an ester, an acid, an alcohol, a quaternary ammonium, a quaternary phosphonium, a sulfonium, a sulfonate or a phosphonate group.

31 Claims, No Drawings

CATALYTIC COMPOSITION FOR DIMERIZING, CO-DIMERIZING AND OLIGOMERIZING OLEFINS

BACKGROUND OF THE INVENTION

1. Field of the Invention

The present invention relates to a catalytic composition used for dimerizing, co-dimerizing and oligomerizing olefins. More particularly, it relates to a composition resulting from at least partly dissolving at least one nickel compound mixed or complexed with a tertiary phosphine or a phoshite carrying a functional group, in a liquid mixture of ionic nature of at least one quaternary ammonium halide and/or at least one quaternary phosphonium halide, at least one aluminum halide and optionally at least one organometallic aluminum compound.

2. Description of the Prior Art

French Patent No. 2,611,700 describes the use of liquids of ionic nature formed from aluminum halides and quaternary ammonium halides as solvents for organometallic nickel complexes to catalyze olefin dimerization. The use of such media, which are not miscible with aliphatic hydrocarbons, in particular with the products from olefin dimerization, enables homogeneous catalysts to be used more effectively. French Patent No. 2,659,871 describes a liquid composition with an ionic nature resulting from bringing quaternary ammonium halides and/or quaternary phosphonium halides into contact with alkylaluminum dihalides and optionally also an aluminum trihalide. That same patent describes the use of such media as solvents for transition metal complexes, in particular nickel complexes containing no nickel-carbon bond, which are transformed into catalysts for olefin oligomerization. In the present text, such media will henceforth be termed "molten salts", as they are liquid at moderate temperatures.

During those studies, it was shown that the most active and most stable nickel catalysts are obtained in "molten salts" constituted by one molar equivalent of an ammonium halide and/or a phosphonium halide with one equivalent and more of an aluminum trihalide, and optionally any quantity of an alkyl aluminum dihalide. That formulation has been shown to be particularly interesting as nickel complexes dissolved in it have high catalytic activity.

It has been shown that under such conditions and when the reaction is carried out in a semi-open system with a continuous olefin supply and continuous separation of the products after decanting, a small but non-negligible proportion of the nickel is extracted in the organic phase.

Further, it has been shown that under the conditions described in French Patent No. 2,611,700, the "phosphine effect", as described by G. Wilke et al., in Ind. Eng. Chem., 1970, 62, No. 12, p. 34, and in U. K. Patent No. 1,058,680, which reports the influence of substituents carried by the phosphorus atom on the mode of enchainment of propylene molecules during catalytic dimerization by nickel, rapidly disappears over time. That unexplained phenomenon has deleterious consequences since it does not produce the desired selectivities.

Further, French Patent No. 2,710,280 shows that adding an aromatic hydrocarbon to a "molten salt" can overcome this problem and result in catalysts with high activity which are more stable and which have a high selectivity for the most highly branched isomers. However, the aromatic hydrocarbon is continuously extracted in the organic phase constituted by the products, which implies that it must be separated and recycled to the reactor.

SUMMARY OF THE INVENTION

It has now been discovered that the use of a tertiary phosphine carrying a functional group or a phosphite carrying a functional group or a nickel complex formed with a tertiary phosphine or a functionalized phosphite that is soluble in the "molten salt" results in catalysts with high activity which are stable over time and wherein the extraction of nickel from the reaction products is reduced to a minimum. This has the result of reducing the consumption of the catalyst and thus of improving the economics of the process.

DETAILED DESCRIPTION OF THE INVENTION

The invention provides a catalytic composition comprising at least one nickel compound mixed or complexed with at least one tertiary phosphine or a phosphite carrying a functional group, at least partly dissolved in a non aqueous medium with an ionic nature ("molten salt" type medium), resulting from bringing at least one aluminum halide (product B) into contact with at least one quaternary ammonium halide and/or at least one quaternary phosphonium halide (product A), the "molten salt" type medium possibly further comprising at least one organometallic aluminum compound (product C).

Thus the "molten salt" type medium, in which the nickel compound mixed or complexed with at least one tertiary phosphine carrying a functional group or at least one phosphite carrying a function group is dissolved, is constituted by mixing:

a) at least one quaternary ammonium and/or quaternary phosphonium halide, more particularly a chloride and/or bromide (product A);

b) at least one aluminum halide (product B); and c) optionally, at least one organometallic aluminum compound (product C).

Preferred quaternary ammonium and/or phosphonium halides that can be used within the context of the invention (product A), are:

Those with general formula $NR^1R^2R^3R^4X$ (with the exception of $NH_4X$), $PR^1R^2R^3R^4X$, $R^1R^2N=CR^3R^4X$ or $R^1R^2P=CR^3R^4X$, where X represents Cl or Br and $R^1$, $R^2$, $R^3$ and $R^4$, which may be identical or different, each represent hydrogen or a hydrocarbyl residue containing 1 to 12 carbon atoms, for example saturated or unsaturated alkyl, cycloalkyl or aromatic groups, aryl groups or aralkyl groups, containing 1 to 12 carbon atoms, it being understood that preferably, only one of substituents $R^1$, $R^2$, $R^3$ and $R^4$ represents hydrogen; or one of the following general formulae:

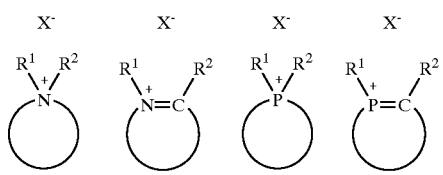

where the nitrogen-containing or phosphorus-containing heterocycles containing 1, 2 or 3 nitrogen and/or phosphorus atoms are constituted by 4 to 10 atoms and X, $R^1$ and $R^2$ are defined as above.

Examples which can be cited are tetrabutyl phosphonium chloride, N-butyl pyridinium chloride, ethylpyridinium bromide, 3-butyl-1-methyl imidazolium chloride, diethylpyrazolium chloride, pyridinium hydrochloride, trimethylphenyl ammonium chloride and 3-ethyl-1-methyl imidazolium chloride. These salts can be used alone or as a mixture.

The aluminum halides used as products B of the invention are essentially aluminum chloride and bromide.

The organometallic aluminum compounds used as optional products C of the invention have general formula $AlR_xX_{3-x}$ in which R is a linear or branched alkyl residue containing 2 to 8 carbon atoms, X is chlorine or bromine and the value of x is 1, 2 or 3. Examples of organometallic aluminum compounds that can be used are isobutylaluminum sesquichloride, ethylaluminum sesquichloride, dichloroisobutyl aluminum, dichloroethyl aluminum and chlorodiethylaluminum.

The components of the "molten salts" as defined above are generally used in A:B mole ratios of 1:0.5 to 1:3, preferably 1:1 to 1:2; product C is used in a mole ratio of at most 100:1 with product B, preferably 0.005:1 to 10:1. However, the components and their proportions must be such that the mixture is liquid at the temperature at which the nickel compound and the functionalized tertiary phosphine or functionalized phosphite are introduced, although the catalytic dimerization reaction Examples of nickel compounds used in the catalytic compositions of the invention are the chloride, bromide, sulfate, carboxylates (for example the 2-ethylhexanoate), phenates and acetyl acetonate. It is also possible to use organometallic nickel complexes which may or may not contain phosphines or phosphites. These nickel complexes are used as a mixture with a functionalized tertiary phosphine or a functionalized phosphite. It is also possible to use nickel complexes that are already complexed with a tertiary phosphine carrying a function or a phosphite carrying a function.

The functional phosphines used as a mixture with (or to complex) the nickel compounds of the invention have general formulae $PR'_1R'_2R'_3$ and $R'_1R'_2P-R'-PR'_1R'_2$, and $R'_3$, which may be identical or different, are alkyl, cycloalkyl, aryl or aralkyl radicals containing 1 to 10 carbon atoms at least one of which carries a functional group such as an amine, a cyclic amine, a nitrogen-containing heterocycle, an ester, an acid, an alcohol, a quaternary ammonium, a quaternary phosphonium, a sulfonium, a sulfonate or a phosphonate and R' is a divalent aliphatic residue containing 1 to 6 carbon atoms.

The functional phosphines can be selected from compounds containing pyridine or imidazole substituents or their quaternized derivatives containing pyridinium or imidazolium substituents that satisfy formulae 1 to 7 defined below.

Examples of functional phosphines carrying a pyridine substituent are 2-dicyclopentylphosphinoethyl-4-pyridine with formula (1), 2-dicyclopentylphosphinoethyl-2-pyridine with formula (2), 2-diisobutylphosphinoethyl-4-pyridine with formula (1b), 2-diisopropylphosphinoethyl-4-pyridin with formula (4) and their quaternization derivatives with formula (3), where R is an alkyl group containing 1 to 10 carbon atoms and X is a weakly co-ordinating anion. Examples of weakly coordinating anions which can be cited are tetrafluoroborate, hexafluorophoshate, tetrachloroaluminate, hexafluoroantimonate, carboxylate anions such as acetate, trifluoroacetate, trifluorosulfonate, and the anions $N(CF_3SO_2)_2^-$ and $C(CF_3SO_2)_3^-$. Examples of quaternization derivatives are 2-dicyclopentylphosphinoethyl-N-ethyl pyridinium tetrafluoroborate with formula (3a), or 2-dicyclopentylphosphinoethyl-N-ethyl pyridinium chloride with formula (3b).

Examples of functional phosphines carrying an imidazole substituent which can be cited are 2-dicyclopentylphosphinoethyl-N-imidazole with formula (5), 2-diisopropylphosphinoethyl-N-imidazole with formula (7), 2-diisobutylphosphinoethyl-N-imidazole with formula (7b) and their quaternization derivatives with formula (6), where R is an alkyl group containing 1 to 10 carbon atoms and X is a weakly coordinating anion (as defined above), such as 2-dicyclopentylphosphinoethyl-1-methyl imidazolium tetrafluoroborate with formula (6a).

The functionalized phosphites used as a mixture with (or to complex the nickel compounds of the invention) have general formulae $P(OR''_1)(OR''_2)(OR''_3)$ and $(-O-R''_5-O-)P(OR''_2)$, where $R''_1$, $R''_2$, $R''_3$ and $R''_5$, which may be identical or different, are aryl or aralkyl radicals at least one of which carries a functional group such as an amine, a cyclic amine, a nitrogen-containing heterocycle, an ester, an acid, an alcohol, a quaternary ammonium, a quaternary phosphonium, a sulfonium, a sulfonate or a phosphonate.

The functional phosphites can be selected from compounds with formulae 9 to 11 described below.

It is possible to use phosphites represented by general formula (9) (where x is 0 to 2), where $Y^+$ can be an organic cation such as a quaternary ammonium or quaternary phosphonium with general formula $NR^1R^2R^3R^4$ and $PR^1R^2R^3R^4$ where $R^1$, $R^2$, $R^3$ and $R^4$, which may be identical or different, each represent hydrogen, an aliphatic (saturated or unsaturated) or aromatic hydrocarbon group containing 1 to 12 carbon atoms; the quaternary ammonium and/or phosphonium ions can also be derivatives of heterocycles containing 1, 2 or 3 nitrogen and/or phosphorus atoms or an alkaline cation such as $Li^+$, $Na^+$ or $K^+$ [formula (9b)].

It is also possible to use phosphites represented by general formula (10), where cation $Y^+$ can be an alkali cation such as $Li^+$, $Na^+$ or $K^+$ [formula (10b)] or an organic cation such as a quaternary ammonium or quaternary phosphonium with general formula $NR^1R^2R^3R^4$ and $PR^1R^2R^3R^4$ where $R^1$, $R^2$, $R^3$ and $R^4$, which may be identical or different, each represent hydrogen, an aliphatic (saturated or unsaturated) or aromatic hydrocarbon group containing 1 to 12 carbon atoms, the quaternary ammonium and/or phosphonium ions can also be derivatives of heterocycles containing 1, 2 or 3 nitrogen and/or phosphorus atoms.

As examples of quaternary ammonium or phosphonium cations that can be found in formulae (9) and (10), can be cited tetrabutylammonium, as in formula (9a) or formula (10a), tetrabutylphosphonium, N-butylpyridinium, ethylpyridinium, 3-butyl-1-methylimidazolium, diethylpyrazolium and trimethylphenylammonium.

Finally, it is possible to use phosphites represented by general formula (11), where anion X is a weakly coordinating anion. Examples of weakly coordinating anions which can be cited are tetrafluoroborate or hexafluorophosphate, as in formula (11a), tetrachloroaluminate, hexafluoroantimonate, carboxylate anions such as acetate or trifluoroacetate, trifluorosultonate, the $N(CF_3SO_2)_2^-$ and $C(CF_3SO_2)_3^-$ and the tetraphenylborate anion and tetraphenylborate a the aromatic rings are substituted.

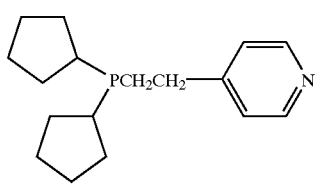

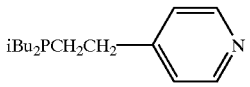

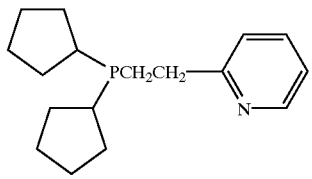

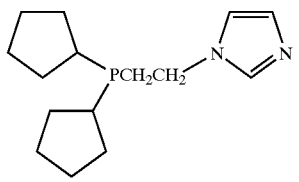

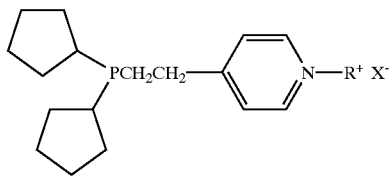

3a X⁻ = BF₄⁻, R = Et
3b X⁻ = Cl⁻  R = Et

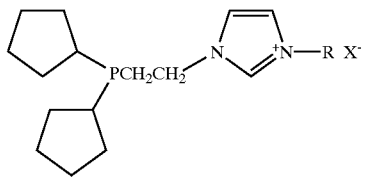

6a X⁻ = BF₄⁻, R = Me

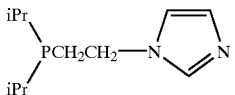

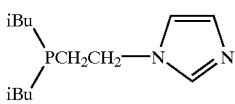

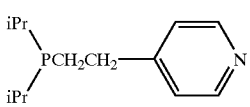

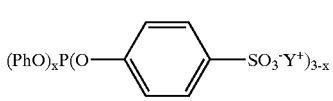

9a x = 0, 1, 2  Y⁺ = NBu₄⁺
9b x = 0, 1, 2  Y⁺ = Li⁺, Na⁺, K⁺

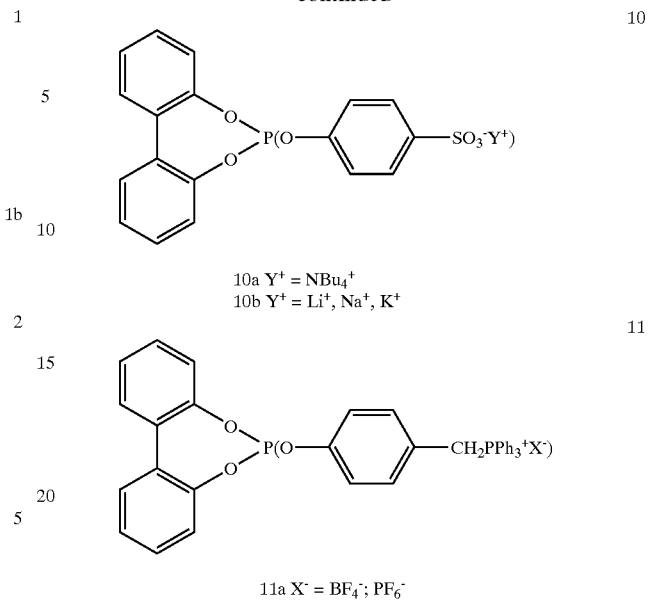

10a Y⁺ = NBu₄⁺
10b Y⁺ = Li⁺, Na⁺, K⁺

11a X⁻ = BF₄⁻; PF₆⁻

As examples of nickel compounds that can be used to constitute the catalytic compositions of the invention, can be cited the complexes [NiCl₂, 1.5 P(2-dicyclopentylethyl-4-pyridine)]₂, [NiCl₂, 2P(2-dicyclopentylethyl-N-ethyl pyridinium tetrafluoroborate)], [Ni₂Cl₄, (2-dicyclopentylphosphinoethyl-N-ethyl pyridinium tetrafluoroborate)₃, 1.5 CH₂Cl₂], NiCl₂, 2 pyridine mixed with at least one equivalent of functionalized tertiary phosphine or functionalized phosphite, nickel chloride mixed with at least one equivalent of 2-dicyclopentylphosphinoethyl-4-pyridine, nickel acetate mixed with at least one equivalent of 2-dicyclopentylphosphinoethyl-4-pyridine, nickel (2-ethyl hexanoate) octoate mixed with at least one equivalent of 2-dicyclopentylphosphinoethyl-4-pyridine and 2-dicyclopentylphosphinoethyl-4-pyridine π-allyl nickel chloride.

The compounds forming part of the catalytic composition of the invention can be mixed in any order. The mixture can be produced by simply bringing them into contact followed by agitation until a homogeneous liquid is formed. This mixture can be produced outside the dimerization or oligomerization reactor or, as is preferable, in the reactor.

More particular olefins that can be dimerized, co-dimerized or oligomerized using the catalytic compositions of the invention are ethylene, propylene, n-butenes and n-pentenes, used alone or as a mixture (co-dimerization), pure or diluted in an alkane, such as those found in cuts from oil refining processes, such as catalytic cracking or steam cracking.

The catalytic olefin dimerization or oligomerization reaction can be carried out in a closed system, in a semi-open system or continuously, with one or more reaction stages. Vigorous agitation must be carried out to ensure good contact between the reactant or reactants and the catalytic mixture. The reaction temperature can be from −40° C. to +70° C., preferably −20° C. to +50° C. It is possible to operate above or below the fusion temperature of the medium, the dispersed solid state not being a limitation to the proper conduct of the reaction. The heat engendered in the reaction can be eliminated using any means known to the skilled person. The pressure can be from atmospheric pressure to 20 MPa, preferably atmospheric pressure to 5 MPa.

The reaction products and the reactant or reactants that has/have not reacted are separated from the catalytic system simply by decanting, then fractionation.

The entire disclosure of all applications, patents and publications, cited above and below, and of corresponding French application 00/01512, filed Dec. 4, 2000, are hereby incorporated by reference.

The following examples illustrate the invention without limiting its scope.

EXAMPLE 1

Preparation of Ionic Solvent 17.5 g (0.1 mole) of 1-butyl-3-methyl imidazolium chloride, 16.3 g (0.122 mole) of sublimed aluminum chloride, 1.6 g (0.0126 mole) of dichloroethyl aluminum was mixed at ambient temperature. A liquid was obtained.

EXAMPLE 2

Preparation of the Complex [$NiCl_2$, 1.5 P(2-dicyclopentylethyl-4-pyridine)]$_2$ 2.37 g of $NiCl_2$, $6H_2O$ and 10 ml of absolute methanol were introduced into a Schlenk tube maintained under an argon atmosphere. After the nickel salt had dissolved, 20 ml of pentane was added. The 2 phases were agitated and 5.33 g of tertiary phosphine with formula (1) (20 mmoles) was added. After 2 hours agitation, the red precipitate was filtered. 5.82 g was obtained. Elemental analysis corresponded to the complex with formula [$NiCl_2$, 1.5 P(2-dicyclopentylethyl-4-pyridine)]$_2$ (M=1085 g; 10.7% by weight of Ni).

EXAMPLE 3

Quaternization of Pyridine in the Complex Described in Example 2

3.72g of the complex described in Example 2 was placed in a Schlenk tube and dichloromethane was added. Then a solution of tetrafluoroborate oxonium in dichloromethane (2.14 g of $Et_3O^+BF_4^-$) was added dropwise. It was agitated for 4 hours, at the end of which period a red solution was obtained. The solvent was evaporated off and 20 ml of ether was added. The red crystalline solid obtained was filtered off. 4.56 g was obtained. Elemental analysis corresponded to the complex with formula: $Ni_2Cl_4(P-N^+EtBF_4^-)_3$, 1.5 $CH_2Cl_2$, where P-N is the ligand with formula (1).

EXAMPLE 4

Propylene Dimerization

A glass reactor provided with a temperature sensor, a magnetic bar in the lower stage (20 ml volume) to ensure proper agitation and a double envelope for circulating a cooling liquid was purged of air and moisture and maintained at an atmospheric pressure of 99% pure propylene. 0.03 mmole of the complex prepared in Example 2 (0.06 mmole of Ni) was introduced then the temperature was reduced to 10° C. and 5 ml of the liquid composition prepared above (Example 1) was injected using a syringe, along with 7 ml of heptane. Agitation was commenced and immediately, propylene absorption was observed. When the non-agitated upper stage was full of liquid, the major portion of the hydrocarbon phase had been extracted. The reaction was stopped after 7 hours (5 extractions). At that time, 175 kg of products per gram of Ni had been produced. Analysis of the different fractions showed that they were composed of 77% of dimers. The composition of the dimers, which was practically identical in all of the fractions, was 67% of 2,3-dimethylbutenes, and 29% of methyl pentenes, the remainder being n-hexenes.

EXAMPLE 5

Propylene Dimerization

The procedure of Example 4 was carried out, with the exception that the molten salt prepared for this purpose was used, and that 0.05 mmole of nickel (2-ethylhexanoate) octoate and 0.5 mmole of 2-dicyclopentylphosphinoethyl-4-pyridine were introduced. The reaction period was 7 hours 15 minutes, at the end of which 5 fractions had been extracted and 220 kg of products per gram of Ni had been produced. The dimer selectivity was 78%. The selectivity for 2,3-dimethylbutenes was 66% in the first fraction and 63% in the final fraction.

EXAMPLE 6

Propylene Dimerization

The procedure of Example 4 was followed, with the exception that the molten salt for this purpose was used, and that 45 mg of the complex prepared in Example 3 was introduced. The reaction period was 7 hours 15 minutes, at the end of which 5 fractions had been extracted and 117 kg of products per gram of Ni had been produced. The dimer selectivity was 74–79%. The selectivity for 2,3-dimethylbutenes was 65% and was constant for the various fractions.

EXAMPLE 7

Comparative

Propylene Dimerization

The procedure of Example 4 was followed, with the exception that the molten salt used was that prepared in Example 1, introducing 0.05 mmole of the complex $NiCl_2$, $2P(cyclohexyl)_3$. The reaction was left for 8 hours 30 minutes, at the end of which 10 fractions had been extracted. 137 kg of products per gram of Ni were produced, with a dimer selectivity of 83%. The selectivity for 2,3-dimethylbutenes was 70% in the first fraction; it dropped to 35% in the third and to 10% in the sixth fraction. It was 6% in the tenth fraction.

EXAMPLE 8

Butene Dimerization

The molten salt prepared in Example 1 was used. The procedure of Example 4 was used with the exception that butene-1 was used instead of propylene. 0.115 mmole (0.23 mmoles of Ni=13.5 mg of Ni) of the complex prepared in Example 2 was introduced into the lower stage of the glass reactor then the temperature was reduced to 10° C. and 5 ml of the salt and 20 ml of heptane were injected under a butene atmosphere. Agitation was commenced and butene absorption was observed. When the non-agitated upper stage was full of fluid, the major portion of the hydrocarbon phase had been extracted. The reaction was stopped after 21 hours (28 extractions). At that moment, 1708 g of butene had been consumed. 76 kg of products per gram of Ni had been produced. Analysis of the different fractions showed that they were composed of 80% of dimers. The ensemble of the organic fractions was treated with 10% nitric acid. 2.25 ml of Ni was found in the nitric acid (X-ray fluorescence determination). A proportion of 19% by weight of nickel (calculated with respect to the nickel introduced) had thus been extracted with the products after 21 hours of reaction.

EXAMPLE 9

Preparation of Ligand with Formula (9a)

26.1 g (65.58 mmole) of tetrabutylammonium 4-hydroxy benzene sulfonate and 100 ml of toluene were introduced into a three-necked flask. It was heated to 140° C. and over 1 hour, 6.82 g (21.8 mmole) of triphenylphosphite and 0.385 g of trioctylamine were added. It was left for another 1 hour at 140° C. then placed under vacuum ($10^{-6}$ mm Hg) for 6 hours at 110° C. The product obtained was analyzed by $^{31}P$ NMR. It was constituted by a mixture of 3 phosphites corresponding to x=0, 1 and 2.

9a  x = 0, 1, 2   $Y^+ = NBu_4^+$

EXAMPLE 10

Butene Dimerization

The molten salt prepared in Example 1 was used. The procedure of Example 8 was followed, with the exception that the complex $NiCl_2$, 2-pyridine (0.2 mmole; 11.8 mg Ni) was used as the catalyst precursor to which 5 equivalents (670 mg) with respect to the nickel of the phosphite with formula (9a) had been added, prepared as described in Example 9. The reaction was stopped after 43.5 hours (22 extractions). At that time, 1428 g of butene had been consumed. 73 kg of products per gram of Ni was produced. Analysis of the different fractions showed that they were composed of 97–99% of dimers. The ensemble of the organic fractions was treated with 10% nitric acid. 1 mg of Ni was found in the nitric acid (X-ray fluorescence determination). A proportion of 8.5% by weight of nickel (calculated with respect to the nickel introduced) had thus been extracted with the products after 43.5 hours of reaction.

EXAMPLE 11

Butene Dimerization

The procedure of Example 10 was followed, with the exception that 1 equivalent (134 mg) of the phosphite with formula (9a) was added with respect to the complex $NiCl_2$, 2-pyridine. The reaction was stopped after 35 hours (12 extractions). At that time, 2102 g of butene had been consumed. 107 kg of products per gram of Ni was produced. Analysis of the different fractions showed that they were composed of 95–97% of dimers. The ensemble of the organic fractions was treated with 10% nitric acid. 1.4 mg of Ni was found in the nitric acid (X-ray fluorescence determination). A proportion of 12% by weight of nickel (calculated with respect to the nickel introduced) had thus been extracted with the products after 35 hours of reaction.

EXAMPLE 12

Comparative

Butene Dimerization

The molten salt prepared in Example 1 was used. The procedure of Example 7 was followed, with the exception that the complex $NiCl_2$, $2P(cyclohexyl)_3$ (0.2 mmole of Ni; 11.8 mg Ni) was used as the catalyst precursor, and 40 ml of heptane. The reaction was stopped after 14.8 hours (9 extractions). A substantial reduction in butene consumption was observed. At that time, 815 g of butene had been consumed. 84 kg of products per gram of Ni was produced. Analysis of the different fractions showed that they were composed of 90–94% of dimers. The ensemble of the organic fractions was treated with 10% nitric acid. 6.2 mg of Ni was found in the nitric acid (X-ray fluorescence determination). A proportion of 52% by weight of nickel (calculated with respect to the nickel introduced) had thus been extracted with the products after 14.8 hours of reaction.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A catalyst composition comprising, at least partly dissolved in a non-aqueous medium with an ionic nature at least one nickel compound mixed or complexed with at least one tertiary phosphine or phosphite each carrying a functional group, said non aqueous medium with an ionic nature comprising at least one aluminum halide (product B) and at least one quaternary ammonium halide and/or at least one quaternary phosphonium halide (product A).

2. A composition according to claim 1, wherein the nickel compound is a chloride, bromide, sulfate, carboxylate, phenate or acetylacetonate.

3. A composition according to claim 1, wherein the tertiary phosphine carrying a functional group has the formula $PR'_1R'_2R'_3$ or $R'_1R'_2P—R'—PR'_1R'_2$, where $R'_1$, $R'_2$ and $R'_3$, which are identical or different, are alkyl, cycloalkyl, aryl or aralkyl radicals containing 1 to 10 carbon atoms at least one of which carries a functional group which is an amine, a cyclic amine, a nitrogen-containing heterocycle, an ester, an acid, an alcohol, a quaternary ammonium, a quaternary phosphonium, a sulfonium, a sulfonate or a phosphonate group and R' is a divalent aliphatic residue containing 1 to 6 carbon atoms.

4. A composition according to claim 3, wherein the tertiary phosphine carrying a functional group is a phosphine containing pyridine or imidazole substituents or a quaternized phosphate with pyridinium or imidazolium substituents.

5. A composition according to claim 4 wherein the tertiary phosphine carrying a pyridine or imidazole substituent is 2-dicyclopentylphosphinoethyl-4-pyridine, 2-dicyclopentylphosphinoethyl-2-pyridine, 2-diisobutylphosphinoethyl-4-pyridine, 2-diisopropylphosphinoethyl-4-pyridine, 2-dicyclopentylphosphinoethyl-N-imidazole, 2-diisopropylphosphinoethyl-N-imidazole or 2-diisobutylphosphinoethyl-N-imidazole.

6. A composition according to claim 4 wherein the tertiary phosphine carrying a pyridinium or imidazolium substituent is a quaternization derivative with one of formulae (3)

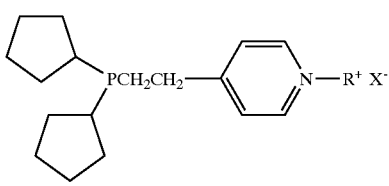

3 or (6)

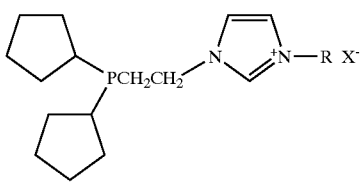

6 where R is an alkyl group containing 1 to 10 carbon atoms and X is a weakly coordinating anion.

7. A composition according to claim 6, wherein the weakly coordinating anion is tetrafluoroborate, hexafluorophosphate, tetrachloroaluminate, hexafluoroantimonate, or a carboxylate anion.

8. A composition according to claim 6, wherein the tertiary phosphine carrying a pyridinium or imidazolium substituent is 2-dicyclopentylphosphinoethyl-N-ethyl pyridinium tetrafluoroborate, 2-dicyclopentylphosphinoethyl-N-ethyl pyridinium chloride or 2-dicyclopentylphosphinoethyl-1-methyl-imidazolium tetrafluoroborate.

9. A composition according to claim 1, wherein the phosphite carrying a functional group has the formula:

$P(OR''_1)(OR''_2)(OR''_3)$ or;

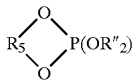

where $R''_1$, $R''_2$, $R''_3$ and $R''_5$, which are identical or different, are aryl or aralkyl radicals wherein at least one carries a functional group.

10. A composition according to claim 9, wherein the phosphite carrying a functional group has formula (9)

9 where x=0 to 2, in which cation Y:
  is sodium, lithium or potassium and the quaternary ammonium and quaternary phosphonium cations have the formulae:
    $N^+R^1R^2R^3R^4$ and $P^+R^1R^2R^3R^4$ where $R^1$, $R^2$, $R^3$ and $R^4$, which are identical or different, each represent hydrogen, a saturated or unsaturated aliphatic or an aromatic hydrocarbon group containing 1 to 12 carbon atoms: or
  contains a heterocycle containing 1, 2 or 3 nitrogen and/or phosphorus atoms.

11. A composition according to claim 9, wherein the phosphite is of formula (10)

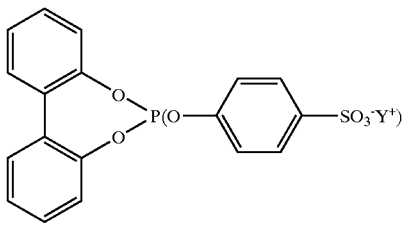

10 where cation Y
  is sodium, lithium, potassium, quaternary ammonium or quaternary phosphonium cations of formulae:
    $N^+R^1R^2R^3R^4$ or $P^+R^1R^2R^3R^4$ where $R^1$, $R^2$, $R^3$ and $R^4$, which are identical or different, each represent hydrogen, a saturated or unsaturated aliphatic or an aromatic hydrocarbon group containing 1 to 12 carbon atoms; or
  a heterocyclic compound containing 1, 2 or 3 nitrogen and/or phosphorus atoms.

12. A composition according to claim 10, wherein the quaternary ammonium or phosphonium is tetrabutylammonium, tetrabutyl-phosphonium, N-butylpyridinium, ethylpyridinium, 3-butyl-1-methyl imidazolium, diethyl-pyrazolium or trimethylphenyl ammonium.

13. A composition according to claim 9, wherein the phosphite has formula (11)

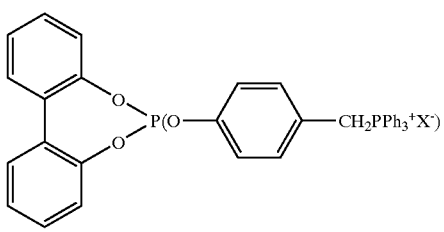

11 where anion X is a weakly coordinating anion.

14. A composition according to claim 13, wherein the weakly coordinating anion is tetrafluoroborate, hexafluorophosphate, tetrachloroaluminate, hexafluoroantimonate, a carboxylate anion, trifluorosulfonate, $N(CF_3SO_2)_2^-$, $C(CF_3SO_2)_3^-$, or tetraphenylborate or tetraphenylborate anions wherein aromatic rings are substituted.

15. A composition according to claim 9, wherein the tertiary phosphite carrying a functional group is a phosphite of formulae (9a), (9b), (10a), (10b) or (11a):

9

9a x = 0,1,2 $Y^+$ = $NBu_4^+$
9b x = 0,1,2 $Y^+$ = $Li^+$, $Na^+$, $K^+$

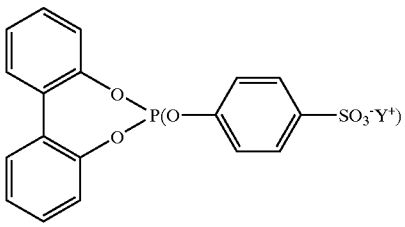

10a Y⁺ = NBu₄⁺
10b Y⁺ = Li⁺, Na⁺, K⁺

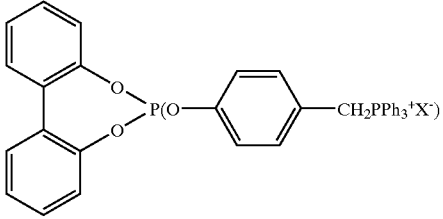

11a X⁻ = BF₄⁻; PF₆⁻

16. A composition according to claim 1, wherein the nickel compound mixed or complexed with at least one tertiary phosphine carrying a functional group is:

[NiCl₂.1.5(2-dicyclopentylphosphino ethyl-4-pyridine)]₂;

[NiCl₂.2(2-dicyclopentylphosphino ethyl-N-ethyl pyridinium tetrafluoroborate)];

[NiCl₄.(2-dicyclopentylphosphinoethyl-N-ethylpyridinium tetrafluoroborate)₃, 1.5CH₂Cl₂];

NiCl₂.2 pyridine mixed with at least one equivalent of functionalized tertiary phosphine or functionalized phosphite;

nickel chloride mixed with at least one equivalent of 2-dicyclopentylphosphinoethyl-4-pyridine;

nickel acetate mixed with at least one equivalent of 2-dicyclopentylphosphinoethyl-4-pyridine;

nickel (2-ethyl hexanoate) octoate mixed with at least one equivalent of 2-dicyclopentylphosphinoethyl-4-pyridine; or 2-dicyclopentylphosphinoethyl-4-pyridine π-allyl nickel chloride.

17. A composition according to claim 1, wherein the quaternary ammonium halide or quaternary phosphonium halide used as product A satisfies:

one of formulae: NR¹R²R³R⁴X with the exception of NH₄X, PR¹R²R³R⁴X, R¹R²N=CR³R⁴X or R¹R²P=CR³R⁴X, where X represents Cl or Br and R¹, R², R³ and R⁴, which are identical or different, each represent hydrogen or a hydrocarbyl residue containing 1 to 12 carbon atoms;

or one of the following nitrogen-containing or phosphorus-containing heterocycles containing 1, 2 or 3 nitrogen and/or phosphorus atoms and 4–10 atoms total in the heterocyclic ring:

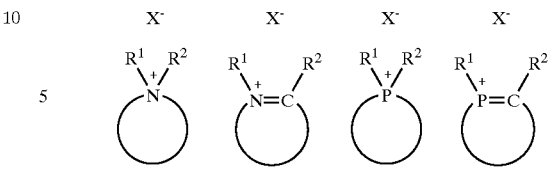

in which X, R¹ and R² are defined as above.

18. A composition according to claim 17, wherein the quaternary ammonium halide or quaternary phosphonium halide is tetrabutyl phosphonium chloride, N-butyl pyridinium chloride, ethylpyridinium bromide, 3-butyl-1-methyl imidazolium chloride, diethylpyrazolium chloride, pyridinium hydrochloride, trimethylphenylammonium chloride or 1-ethyl-3-methyl imidazolium chloride.

19. A composition according to claim 1, wherein the aluminum halide used as product B is aluminum chloride or bromide.

20. A composition according to claim 1, wherein products A and B are used in an A:B mole ratio of 1:0.5 to 1:3.

21. A composition according to claim 1, wherein the non-aqueous medium with an ionic nature further comprises a product C, consisting of at least one organometallic aluminum compound.

22. A composition according to claim 21, wherein the organometallic aluminum compound used as optional product C has formula $AlR_xX_{3-x}$ where R is a linear or branched alkyl residue containing 2 to 8 carbon atoms, X is chlorine or bromine and the value of x is 1, 2 or 3.

23. A composition according to claim 21, wherein product C is isobutylaluminum sesquichloride, ethylaluminum sesquichloride, dichloroisobutylaluminum, dichloroethylaluminum, or chlorodiethylaluminum.

24. A composition according to claim 21, wherein product C is used in a mole ratio of at most 1:100 with product B.

25. A process for dimerizing, co-dimerizing or oligomerizing at least one olefin, comprising contacting said olefin with a composition according to claim 1.

26. A process according to claim 25, wherein the dimerization, co-dimerization or oligomerization reaction is carried out in a closed system, in a semi-open system or in a continuous system, with one or more reaction stages, with agitation and at a temperature of −40° C. to +70° C.

27. A process according to claim 26, wherein the olefins are ethylene, propylene, n-butenes and n-pentenes, used alone or as a mixture, pure or diluted by an alkane.

28. A process according to claim 25, wherein the olefins are contained in cuts from oil refining processes.

29. A composition according to claim 6, wherein the weakly coordinating anion is acetate, trifluoroacetate, trifluorosulfonate, $N(CF_2SO_2)_2^-$ or $C(CF_3SO_2)_3^-$.

30. A composition according to claim 9, wherein the functional group on the phosphite is an amine, a cyclic amine, a nitrogen containing heterocycle, an ester, an acid, an alcohol, a quaternary ammonium, a quaternary phosphonium, a sulfonium, a sulfonate or a phosphonate group.

31. A composition according to claim 14, wherein the carboxylatic anion is acetate or trifluoroacetate.

* * * * *

UNITED STATES PATENT AND TRADEMARK OFFICE
CERTIFICATE OF CORRECTION

PATENT NO. : 6,706,657 B2
DATED : March 16, 2004
INVENTOR(S) : Dominique Commereuc et al.

It is certified that error appears in the above-identified patent and that said Letters Patent is hereby corrected as shown below:

<u>Column 13,</u>
Line 28, reads "NiCl$_2$. 1.5" should read -- NiCl$_2$· 1.5 --
Line 29, reads "NiCl$_2$.2" should read -- NiCl$_2$·2 --
Line 32, reads "NiCl$_4$." should read -- Ni$_2$Cl$_4$· --

Signed and Sealed this

Eleventh Day of January, 2005

JON W. DUDAS
*Director of the United States Patent and Trademark Office*